US00PP08810P

United States Patent [19]

VandenBerg

[11] Patent Number: Plant 8,810

[45] Date of Patent: Jun. 28, 1994

[54] CHRYSANTHEMUM PLANT NAMED DARK RED CONGA

[75] Inventor: Cornelis P. VandenBerg, Salinas, Calif.

[73] Assignee: Yoder Brothers, Inc., Barberton, Ohio

[21] Appl. No.: 41,452

[22] Filed: Apr. 1, 1993

[51] Int. Cl.[5] ..... A01H 5/00

[52] U.S. Cl. ..... Plt./82.5

[58] Field of Search ..... Plt. 82.5

[56] References Cited

U.S. PATENT DOCUMENTS 4,616,099 10/1986 Sparkes ..... 800/1

OTHER PUBLICATIONS

Searle, S. A., et al, (1968) "Use of Gamma and X-Rays" *Chrysanthemums the Year Round,* Blandford Press, Ltd., London pp. 27–29; 321–327.

Broertjes, C., (1966) "Mutation Breeding of Chrysanthemums" *Euphytica* (15) 156–162.

Broertjes, C., et al, (1980) "A Mutant of a Mutant of a Mutant of a . . . , Irradiation of Progressive Radiation-Induced Mutants in a Mutation Breeding Programme with *Chrysanthemum morifolium*" *Euphytica* (29) pp. 525–530.

Chan, A. P., (1966) "Chrysanthemum and Rose Mutations Induced by X-Rays" J. Am. Soc. Hort. Sci., (88) pp. 613–620.

Broertjes, C., et al., (1978) "Chrysanthemum" *Application of Mutation Breeding Methods in the Improvement of Vegetatively Propagated Crops,* Elsevier Sci. Pub. Co., New York, pp. 162–175.

Dowrick, G. J., et al., (1966) "The Induction of Mutations in Chrysanthemum Using X and Gamma Radiations", *Euphytica* (15) pp. 204–210.

Gosling, S. G., (Ed) (1979) "Sporting and Irradiation" *The Chrysanthemum Manual,* Nat. Chrysanth. Soc., Whetstone, London pp. 329–336.

Sigurbjornsson, B., "Chapter 8, Induced Mutations", *Crop Breeding,* 1983, ASA, CSSA, pp. 153–176.

*Primary Examiner*—James R. Feyrer

*Attorney, Agent, or Firm*—Foley & Lardner

[57] ABSTRACT

A Chrysanthemum plant named Dark Red Conga particularly characterized by its flat capitulum form; daisy capitulum type; dark red ray floret color; diameter across face of capitulum of 64 to 79 mm when fully opened, when grown as a single stem spray cut mum; photoperiodic flowering response of 49 to 55 days after start of short days when grown in Salinas, Calif.; flowering response in Bogota, Colombia is 65 to 68 days; plant height is 66 to 94 cm when grown in Salinas with 11 to 18 long days prior to start of short days; height is 91 to 94 cm when grown in Bogota with 15 to 21 long days prior to start of short days; peduncle length of the first lateral at flowering after removing the apical bud and without growth regulator applications is 3 to 8 cm when grown in Salinas, and 13 cm when grown in Bogota; peduncle length of the fourth lateral at flowering is 5 to 10 cm when grown in Salinas, and 15 cm when grown in Bogota; and excellent tolerance to low night temperatures for bud initiation and flower development.

1 Drawing Sheet

The present invention comprises a new and distinct cultivar of Chrysanthemum, botanically known as *Dendranthema grandiflora,* and referred to by the cultivar name Dark Red Conga.

Dark Red Conga, identified as 3462 (87-434B03), is a product of a mutation induction program. The new cultivar was discovered and selected by Cornelis P. VandenBerg on Oct. 25, 1990, in a controlled environment in Salinas, Calif., as one flowering plant within a flowering block established as rooted cuttings from stock plants which had been exposed as unrooted cuttings to an X-ray source of 1750 rads in Fort Myers, Fla., on May 3, 1990.

The irradiated parent cultivar was the cultivar identified as Conga, disclosed in U.S. Plant Pat. No. 8,105, and described as a spray cut mum with flat capitulum form; daisy capitulum type; dark red-purple ray floret color; diameter across face of capitulum of 64 to 79 mm when fully opened; flowering response period of 49 to 53 days after start of short days in Salinas, Calif., and 62 to 68 days in Bogota, Colombia; plant height of 71 to 99 cm when grown in Salinas with 6 to 18 long days prior to start of short days, and 91 to 102 cm when grown in Bogota with 14 to 21 long days prior to start of short days; and excellent tolerance to low night temperatures for bud initiation and flower development. The foregoing description of Conga has a somewhat wider range of measurements than the description of Conga in the noted plant patent. This is based on continued flowering trials of Conga after preparing and filing the patent application for Conga.

The irradiation program resulting in Dark Red Conga had as its primary objective the expansion of ray floret color ranges of the parent cultivar Conga. The irradiation program comprised irradiating cuttings of the parent cultivar at irradiation levels of 1500, 1750 and 2000 rads. A total of 882 cuttings harvested from a total of 225 irradiated plants were planted on Aug. 27, 1990, Aug. 13, 1990 and Aug. 13, 1990, respectively. Of these, 9 initial selections were made, which selections were then revegetated and reflowered. Three consecutive flowerings resulted in discarding 7 of the original 9 selections on Jul. 26, 1991, while 2 codes were retained as PI (Possible Introduction) status. The two retained codes were further tested in Salinas, Calif., and in Bogota, Colombia, ultimately resulting in the decision to introduce both of the remaining selections as Dark Red Conga and Cherry Conga. The latter is disclosed in a pending application.

The first act of asexual reproduction of Dark Red Conga was accomplished when vegetative cuttings were taken from the original selection in December 1990 in a controlled environment in Salinas, Calif., by technicians working under supervision of Cornelis P. VandenBerg.

Horticultural examinations of controlled flowerings of successive plantings has shown that the unique combination of characteristics as herein disclosed for Dark Red Conga are firmly fixed and are retained through successive generations of asexual reproduction.

Dark Red Conga has not been observed under all possible environmental conditions. The phenotype may vary significantly with variations in environment such as temperature, light intensity and daylength, without, however, any variance in genotype.

The following observations, measurements and comparisons describe plants grown in Salinas, Calif. and in Bogota, Colombia, under greenhouse conditions which approximate those generally used in commercial greenhouse practice. The low night temperature tolerance was determined in repeated flowerings in Bogota, Colombia, at temperatures as low as 5°-10° C.

The following traits have been repeatedly observed and are determined to be basic characteristics of Dark Red Conga, which, in combination, distinguish this Chrysanthemum as a new and distinct cultivar:

1. Flat capitulum form.
2. Daisy capitulum type.
3. Dark red ray floret color.
4. Diameter across face of capitulum of 65 to 79 mm when fully opened, when grown as a single stem spray cut mum.
5. Photoperiodic flowering response to short days when grown in Salinas, Calif., is 49 to 55 days after start of short days. Flowering response in Bogota, Colombia is 65 to 68 days.
6. Plant height is 66 to 94 cm when grown in Salinas with 11 to 18 long days prior to start of short days; height is 91 to 94 cm when grown in Bogota with 15 to 21 long days prior to start of short days.
7. Peduncle length of the first lateral at flowering after removing the apical bud and without growth regulator applications is 3 to 8 cm when grown in Salinas, and 13 cm when grown in Bogota. Peduncle length of the fourth lateral at flowering is 5 to 10 cm when grown in Salinas, and 15 cm when grown in Bogota.
8. Excellent tolerance to low night temperatures for bud initiation and flower development.

The accompanying color photographic drawing is a front view of a single stem cut spray mum of Dark Red Conga, with the colors being as nearly true as possible with illustrations of this type.

Of the commercial cultivars known to the inventor, the most similar in comparison to Dark Red Conga is the parent cultivar Conga. All traits of Dark Red Conga are similar to those of Conga, except for the ray floret color and the plant height. The ray floret color of Dark Red Conga is dark red, while the ray floret color of Conga is described as dark red-purple. In most of the flowering trials in California, the plant height of Dark Red Conga has been 5 to 8 cm shorter when compared to the plant height of Conga when plants of the respective cultivars are grown side by side.

In the following description color references are made to the Royal Horticultural Society Colour Chart. The actual color of the ray florets of Dark Red Conga is not precisely represented in the R.H.S. Colour Chart, and the values given are those believed to be closest to the actual color of Dark Red Conga. The color values were determined on plant material grown as a single stem spray cut mum in Salinas, Calif. on Dec. 16, 1992.

Classification:

*Botanical.*—*Dendranthema grandiflora* cv Dark Red Conga.

*Commercial.*—Flat daisy cut spray mum.

INFLORESCENCE

A. Capitulum:

*Form.*—Flat.

*Type.*—Daisy.

*Diameter across face.*—64 to 79 mm when fully opened.

B. Corolla of ray florets:

*Color (general tonality from a distance of three meters).*—Dark red.

*Color (upper surface).*—53B.

*Color (under surface).*—22C, slightly streaked with 34D. Shape: Flat, straight.

C. Corolla of disc florets:

*Color (mature).*—14A.

*Color (immature).*—14A, strongly overlaid with 144B.

D. Reproductive organs:

*Androecium.*—Present on disc florets only; no pollen.

*Gynoecium.*—Present on both ray and disc florets.

PLANT

A. General appearance:

*Height.*—66 to 94 cm when grown in Salinas with 11 to 18 long days prior to start of short days; height is 91 to 94 cm when grown in Bogota with 15 to 21 long days prior to start of short days.

B. Foliage:

*Color (upper surface).*—147A.

*Color (under surface).*—147B.

I claim:

1. A new and distinct Chrysanthemum plant named Dark Red Conga, as described and illustrated.

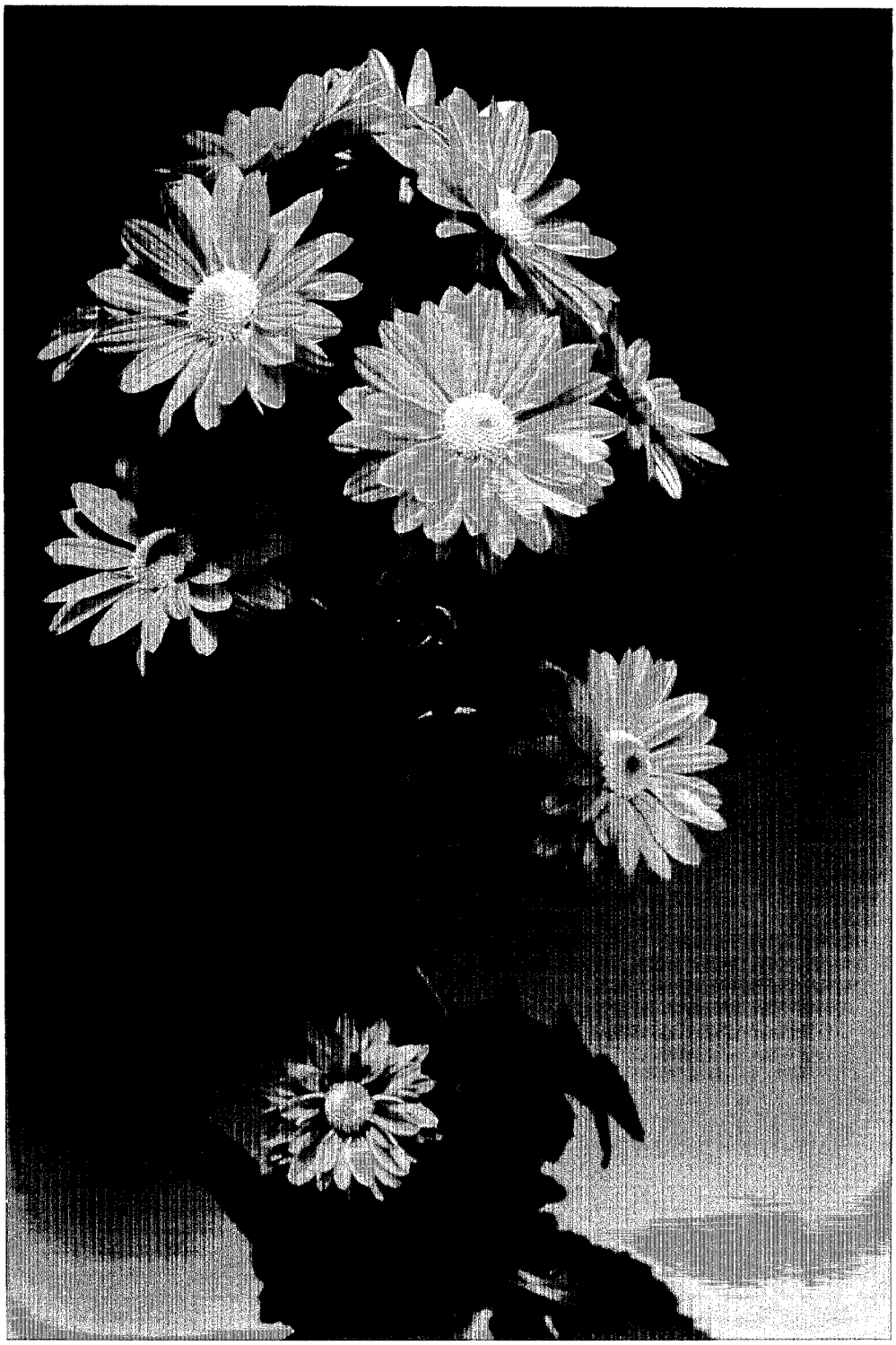

* * * * *